(12) United States Patent
Belen'Kill et al.

(10) Patent No.: US 6,184,426 B1
(45) Date of Patent: Feb. 6, 2001

(54) ADDITION OF HYDROFLUOROCARBONS TO FLUOROOLEFINS

(75) Inventors: Gennadii G. Belen'Kill, Moscow (RU); Viacheslav A. Petrov, Hockessin, DE (US); Paul R. Resnick, Cary, NC (US)

(73) Assignee: DISA, Geneva (CH)

( * ) Notice: Under 35 U.S.C. 154(b), the term of this patent shall be extended for 0 days.

(21) Appl. No.: 09/381,539

(22) PCT Filed: Mar. 19, 1998

(86) PCT No.: PCT/US98/05541

§ 371 Date: Sep. 21, 1999

§ 102(e) Date: Sep. 21, 1999

(87) PCT Pub. No.: WO98/42645

PCT Pub. Date: Oct. 1, 1998

(30) Foreign Application Priority Data

Mar. 24, 1997 (RU) .................................................. 97106117

(51) Int. Cl.$^7$ .................................................. C07C 21/18
(52) U.S. Cl. .................................................. 570/172
(58) Field of Search ................................................. 570/172

(56) References Cited

U.S. PATENT DOCUMENTS

| 5,162,594 | 11/1992 | Krespan | 570/126 |
|---|---|---|---|
| 5,227,547 * | 7/1993 | Ohnishi et al. | 570/172 |
| 5,326,913 * | 7/1994 | Aoyama et al. | 570/172 |
| 5,608,126 * | 3/1997 | Morikawa | 570/172 |
| 5,929,293 | 7/1999 | Krespan et al. | 570/153 |

FOREIGN PATENT DOCUMENTS

WO 97/02227   1/1997 (WO) .

OTHER PUBLICATIONS

V.A. Petrov et al., Electrophilic Alkylation of Fluroolefins With 1,1,1–Trifluoroethane, *Instituted of Heteroorganic Compounds*, 9, 1513–1515, Sep., 1980.

Haszeldine et al., Reaction of Hexafluoropropene with Halogenoalkanes, *Journal of Fluorine Chemistry*, 21,No. 2, 253–259, 1982.

G.G. Belen'Kii et al., Chemistry Reviews, *Electrophilic Additions*, pp. 194–197, vol. 5, 1984.

* cited by examiner

*Primary Examiner*—Alan Siegel

(57) ABSTRACT

A process is disclosed for forming adducts of the formula: $RR^1R^2CCR^1R^2F$ or $(FR^1R^2CCRR^2CH_2)_2$ where R is $CH_3$, $CH_2F$, or $F(CF_2)_nCH_2CH_2$ (where n is an integer from 1 to 10) each $R^1$ is H, Cl, F or $CF_3$ and each $R^2$ is H, F or $CF_3$. The process in reacting a saturated compound of the formula RF with an olefin of the formula $R^1R^2C=CR^1R^2$ in the liquid phase in the presence of antimony pentafluoride catalyst (provided that when $(FR^1R^2CCR^1R^2CH_2)_2$ is formed, the saturated compound is $CH_3CHF_2$ or $CH_2FCH_2F$ and anhydrous HF is present).

2 Claims, No Drawings

ADDITION OF HYDROFLUOROCARBONS TO FLUOROOLEFINS

This application represents a national filing under 35 USC 371 of International Application No. PCT/US98/05541 filed Mar. 19, 1998, and claims priority of Russian application No. 97106117 filed Mar. 24, 1997.

FIELD OF THE INVENTION

This invention concerns a process for the antimony pentafluoride catalyzed addition of hydrofluorocarbons across the carbon—carbon double bond of fluoroolefins.

BACKGROUND

Processes for the addition of 1,1,1-trifluoroethane to fluorinated olefins using antimony pentafluoride as a catalyst have been described (see G. G. Belen'kii and L. S. German, Soviet Scientific Reviews, Sect. B, pp. 195–6, M. E. Volpin ed., (Harwood Academic Publishers, 1984). Processes for the addition of trifluoromethanes, including $CHF_3$, to certain fluorinated olefins using aluminum chlorofluoride as a catalyst have also been described (see U.S. patent application Ser. No. 60/000,720 and International Application No. PCT/US96/10872). Hydrofluorocarbons can be prepared by both processes.

Hydrofluorocarbon products are useful as refrigerants, fire extinguishants, heat transfer media, propellants, foaming agents, gaseous dielectrics, sterilant carriers, polymerization media, particulate removal fluids, carrier fluids, buffing abrasive agents, displacement drying agents and power cycle working fluids. There is an interest in developing more efficient processes for the manufacture of hydrofluoroalkanes.

SUMMARY OF THE INVENTION

A process is provided for forming an adduct of the formula $RR^1R^2CCR^1R^2F$ or $(FR^1R^2CCRR^2CH_2)_2$ wherein R is selected from the group consisting of $CH_3$, $CH_2F$, $C_2H_4F$ and $F(CF_2)_nCH_2CH_2$ where n is an integer from 1 to 10, each $R^1$ is independently selected from the group consisting of H, Cl, F and $CF_3$ and each $R^2$ is independently selected from the group consisting of H, F and $CF_3$. The process comprises reacting a saturated compound of the formula RF with an olefin of the formula $R^1R^2C=CR^1R^2$ in the liquid phase in the presence of antimony pentafluoride catalyst; provided that when $(FR^1R^2CCR^1R^2CH_2)_2$ is formed, the saturated compound is $CH_3CHF_2$ or $CH_2FCH_2F$ and anhydrous HF is present.

DETAILED DESCRIPTION OF THE INVENTION

This invention provides a liquid phase process for the addition of (a) saturated compounds of the formula RF, where R is selected from the group consisting of $CH_3$, $CH_2F$, $C_2H_4F$ and $F(CF_2)_nCH_2CH_2$, where n is an integer from 1 to 10, to (b) olefins of the formula $R^1R^2C=CR^1R^2$ where each $R^1$ is independently selected from the group consisting of H, Cl, F and $CF_3$ and each $R^2$ is independently selected from the group consisting of H, F and $CF_3$; to form adducts of the formula $RR^1R^2CCR^1R^2F$ or $(FR^1R^2CCR^1R^2CH_2)_2$ in the presence of antimony pentafluoride catalyst (provided that when $(FR^1R^2CCR^1R^2CH_2)_2$ is formed, the saturated compound is $CH_3CHF_2$ or $CH_2FCH_2F$ and anhydrous HF is present).

Examples of olefins of the formula $R^1R^2C=CR^1R^2$ which can be used in the process of this invention include $CF_2=CF_2$, $CF_3CF=CF_2$, $CClF=CF_2$, $CClF=CClF$, $CHF=CF_2$, $CH_2=CF_2$, $CF_3CH=CF_2$, $CHF=CFCF_3$ and $CH_2=C(CF_3)CF_3$. Some of the olefins are commercially available, the others can be prepared by known methods.

Examples of saturated compounds of the formula RF which can be used in the process of this invention include $CH_3F$, $CH_2F_2$ and $CH_3CHF_2$.

Solvents or diluents may be employed in the process of the present invention. The solvent or diluent is selected so that it will not be reactive in the process or lead to the deactivation of the antimony fluoride catalyst. Suitable solvents or diluents may be selected from the group consisting of perfluoroalkanes or perfluoroethers (e.g., perfluorocyclobutane); the cyclic dimer of hexafluoropropene (i.e., the isomeric perfluorodimethylcyclobutanes); perfluoroethers or perfluoro tertiary amines. Preferred on the basis of its ready availability to those skilled in the art is the cyclic dimer of hexafluoropropene.

In one embodiment a one to one adduct of the saturated compound and the olefin is formed. It is noted in this regard that the saturated compounds of the formula $F(CF_2)_nCH_2CH_2F$ can themselves be produced as one to one adducts. For example, the addition reaction of $CH_2FCH_2F$ to $CF_2=CF_2$ can be used to produce $F(CF_2)_2CH_2CH_2F$.

In a second embodiment of this invention the addition of the hydrofluorocarbons $CH_3CHF_2$ and/or $FCH_2CH_2F$ to olefins of the formula $R^1R^2C=CR^1R^2$ in the presence of antimony pentafluoride can be done in the presence of anhydrous HF. The molar ratio of $HF:SbF_5$ is in the range of 10:1 to 40:1, preferably 20:1. The addition product or adduct is $(FR^1R^2CCR^1R^2CH_2)_2$. Without wishing to be bound by theory, it is believed that when $CH_3CHF_2$ is used it isomerizes to $FCH_2CH_2F$ before reaction with the olefin.

When the addition product (adduct) contains chlorine, the chlorine can be removed by either reaction with HF in the presence of a fluorination catalyst (e.g., $Cr_2O_3$) or by reaction with hydrogen in the presence of a hydrogenation catalyst (e.g., palladium supported on carbon). The adduct is thereby converted from a hydrochlorofluorocarbon to a hydrofluorocarbon.

The temperature employed in the process of the present invention typically ranges from about −10° C. to about 100° C. The preferred temperature range is from about 0° C. to 80° C.

Reaction time is not critical and typically ranges from about 5 seconds to about 24 hours. From about 1 to 16 hours, are usually sufficient.

The pressure employed in the reaction is not critical. The reaction is normally run at pressures in the range of from 0 to 300 psig (101 kPa to 2169 kPa). Autogenous pressures are usually employed; however the pressure should not be allowed to rise above 300 psig when using tetrafluoroethylene because of safety considerations.

Where the reaction conditions are heterogeneous, some degree of agitation is often desirable.

Since the catalysts are water sensitive, reagents and equipment should be dried before use.

The proportion of catalyst to the olefin reactant is typically from about 0.01:1 to about 0.5:1; a range of from 0.1:1 to about 0.5:1 is preferred.

The proportion of saturated compound to olefin is preferably at least about preferably 1:1, when forming $RR^1R^2CCR^1R^2F$ and preferably at least about 2:1 when forming $(FR^1R^2CCR^1R^2CH_2)_2$. Of note are embodiments which use saturated compounds as a solvent such that they are present in substantial excess.

The reaction can be done in batch, semi-batch, semi-continuous or continuous modes in one or more reaction vessels. On a laboratory scale, the reaction can be done in shaker tubes, where all reagents are combined before the reaction vessel is sealed and the reaction begun. It can also be done in autoclaves equipped with an agitator. Product(s) may be isolated by standard chemical engineering techniques, e.g., fractional distillation.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Example 1

$CH_2F_2 + CF_2=CF_2 \rightarrow CH_2FCF_2CF_3$

Difluoromethane (39.0 g, 0.75 mol), antimony pentafluoride (45 g, 0.2 mol) and tetrafluoroethylene (30.0 g, 0.3 mol) were added to a 250 mL steel autoclave. The reaction mixture was stirred at 50° C. for 8 hours, additional tetrafluoroethylene (30.0 g, 0.3 mol) added, and stirring was maintained at 50° C. for 8 more hours. The gaseous reaction products were condensed in a trap, then distilled to yield $CH_2FCF_2CF_3$ (75 g, 80% yield), b.p. 0–1° C.

$^{19}F$ NMR (δ, ppm, relative to $CF_3CO_2H$) of $CH_2F^CCF_2^BCF_3^A$: A 8.5, B 51.5, C 167.6, $J_F^{A-C}$ is 9 Hz, $J_F^B{}_{-H}$ is 12 HZ, $J_F^C{}_{-H}$ is 45 Hz. $^1H$ NMR (δ, ppm, relative to TMS): 5.26 ($CH_2$).

Comparative Example A $CH_2F_2 + CF_2=CF_2 \rightarrow$ No Reaction)

Difluoromethane (26 g), aluminum chlorofluoride ($AlCl_xF_y$, where x+y=3, 5 g) and tetrafluoroethylene (30 g) were added to a 400 mL Hastelloy™ nickel alloy shaker tube. The aluminum chlorofluoride was prepared by the reaction of $AlCl_3$ and $CCl_3F$ according to the method described in U.S. Pat. No. 5,162,594, column 4, lines 35–57. The reaction mixture was agitated at 25° C. for 12 hours. No reaction was detected.

Example 2

$CH_2F_2 + CF_2=CFCF_3 \rightarrow CH_2FCF(CF_3)_2$

Difluoromethane (39.0 g, 0.75 mol), antimony pentafluoride (45 g, 0.2 mol) and perfluoropropylene (66 g, 0.44 mol) were added to a 250 mL steel autoclave. The reaction mixture was stirred at 80° C. for 20 hours. The reaction products were condensed in a trap, then distilled to yield $CH_2FCF(CF_3)_2$ (80 g, 90% yield), b.p. 22–24° C.

$^{19}F$ NMR (δ) of $CH_2F^CCF^B(CF_3^A)_2$: $F^A$ 0.5, $F^B$ 114, $F^C$ 167.5, $J_F^A{}_{-F}{}^B$ is 7 Hz, $J_F^A{}_{-F}{}^C$ is 9.5 Hz, $J_F^C{}_{-F}{}^B$ is 12.5 Hz, $J_F^A{}_{-H}$ is 11 Hz. $^1H$ NMR (δ): 5.25 ($CH_2$), $J_F^C{}_{-H}$ is 45 Hz, $J_F^B$-H is 16 Hz. Mass spectrum (m/z, assignment, %): 201 (M-H)+0.03, 183 (M-F)+2.04, 163 ($C_4HF_6$)+1.4, 150 ($C_3F_6$)+34.4, 133 ($C_3H_2F_5$)+3.4, 131 ($C_3F_5$)+6.3, 119 ($C_2F_5$)+4.4, 114 ($C_3H_2F_4$)+229, 113 ($C_3HF_4$)+27.3, 100 ($C_2F_4$)+22.6, 69 ($CF_3$)+100.

Example 3

$CH_3F + CF_2=CF_2 \rightarrow CH_3CF_2CF_3$

Fluoromethane (35.0 g), antimony pentafluoride (15 g) and tetrafluoroethylene (50 g) were added to a 400 mL Hastelloy™ nickel alloy shaker tube. The reaction mixture was agitated at 25° C. for 6 hours followed by agitation at 50° C. for 10 hours. The reaction products were condensed in a dry-ice trap, then distilled to yield 99% pure $CH_3CF_2CF_3$ (HFC-245cb, 45 g), b.p. −13 to −12° C. The yield of HFC-245cb was 67%.

Comparative Example B $CHF_3 + CF_2=CF_2 \rightarrow$ PTFE

Trifluoromethane (21 g), antimony pentafluoride (7 g) and tetrafluoroethylene (30 g) were added to a 400 mL Hastelloy™ nickel alloy shaker tube. The reaction mixture was agitated at 25° C. for 12 hours. The only product isolated was polytetrafluoroethylene (PTFE, 15 g).

Example 4

$CH_3F + CF_2=CFCF_3 \rightarrow (CF_3)_2CHF + (CF_3)_2CFCH_3 + (CF_3)_2CFC(CH_3)_3 + (CF_3)_2CFC_2H_5$ Fluoromethane (20 g), antimony pentafluoride (15 g) and hexafluoropropylene (75 g) were added to a 400 mL Hastelloy™ nickel alloy shaker tube. The reaction mixture was agitated at 50° C. for 14 hours. The reaction products were condensed in a dry-ice trap, then distilled to yield a mixture (68 g) containing, based on $^1H$ and $^{19}F$ NMR, 66% $(CF_3)_2CHF$, 11% $(CF_3)_2CFCH_3$, 5% $(CF_3)_2CFC_2H_5$, 9% $(CF_3)_2CFC(CH_3)_3$. The yield of $(CF_3)_2CFCH_3$ was 4%.

Example 5

$CH_3F + CClF=CF_2 \rightarrow ClCF_2CF_2CH_3 + CF_3CF_2CH_3 + CF_3CClFCH_3$

Fluoromethane (17 g), antimony pentafluoride (15 g) and chlorotrifluoroethylene (59 g) were added to a 400 mL Hastelloy™ nickel alloy shaker tube. The reaction mixture was agitated at 50° C. for 12 hours. The reaction products were condensed in a dry-ice trap, then distilled to yield a mixture (12 g) containing, based on $^1H$ and $^{19}F$ NMR, 87.5% $ClCF_2CF_2CH_3$, 6.5% $CF_3CF_2CH_3$, 4% $CF_3CFClCH_3$ and 1% unidentified product. The yield of chlorofluoropropanes was 17.4%.

Example 6

$CH_3F + CHF=CF_2 \rightarrow CH_3CHFCF_3 + CH_2FCF_3$

Fluoromethane (10 g), antimony pentafluoride (10 g) and trifluoroethylene (24 g) were added to a 400 mL Hastelloy™ nickel alloy shaker tube. The reaction mixture was agitated at 25° C. for 14 hours. The reaction products were condensed in a dry-ice trap, then distilled to yield a mixture (12 g, b.p. 0 to 2° C.) containing, based on $^1H$ and $^{19}F$ NMR, 90% $CH_3CHFCF_3$ and 10% $CH_2FCF_3$. The yield of $CH_3CHFCF_3$ was 38.6%.

Example 7

$CH_2F_2 + CClF=CClF \rightarrow CH_2ClCF_2CF_2Cl$

Difluoromethane (18 L, 0.7 mol), antimony pentafluoride (22 g, 0.1 mol) and 1,2-dichlorodifluoroethylene (26.6 g, 0.2 mol) were added to a 250 mL steel autoclave. The reaction mixture was stirred at room temperature for 8 hours followed by heating the autoclave in a boiling water bath. The reaction products were condensed in a trap cooled to −78° C. Excess difluoromethane was separated by distillation. The residue was washed with water, dried and distilled to give in 32% yield $CH_2ClCF_2CF_2Cl$ (12 g, b.p. 62° C. to 64° C.).

$^{19}F$ NMR (δ) of $CH_2ClCF_2^BCF_2^ACl$: −50 s ($2F^A$): 41.5 t ($2F^B$). $^1H$ NMR (δ): 3.8; $J_{[H-F]}^B$ is 14 Hz; Mass spectrum (m/z, assignment, %): 184 ($M^+$, $C_3H_2Cl_2F_4^+$, 0.5); 165 (M-F, $C_3H_2Cl_2F_3^+$, 0.3); 149 (M-Cl, $C_3H_2ClF_4^+$, 17.7): 99 ($C_2H_2ClF_2^+$, 100); 85 ($CClF_2^+$, 33); 64 ($C_2H_2F_2^+$, 12).

Example 8

$CH_3CHF_2 + CF_2=CF_2 \rightarrow CH_3CHFCF_2CF_3 + CH_2FCH_2CF_2CF_3$ 1,1-Difluoroethane (53 g, 0.8 mol), antimony pentafluoride (44 g, 0.2 mol) and tetrafluoroethylene (8.5 L, 0.3 mol)

were added to a 250 mL steel autoclave. The reaction mixture was stirred at 40° C. to 50° C. for 10 hours. The reaction products were bubbled through a gas-washing bottle containing water and condensed in a trap cooled to −78° C. Excess 1,1-difluoroethane was separated by distillation. The residue was washed with water, dried and distilled to yield a mixture in 40% yield (20 g, b.p. 23° C. to 27° C.) containing $CH_3CHFCF_2CF_3$ (89%) and $CH_2FCH_2CF_2CF_3$ (11%).

$^{19}$F NMR (δ) of $CH_3{}^1CH^2F^DCF^AF^BCF_3{}^C$: 7.5 (3F$^A$); 55 (F$^A$, F$^B$, AB-system); 120 (F$^D$); $J_F{}^C{}_F{}^D$ is 10 Hz; $J_F{}^A{}_F{}^B$ is 230 Hz; $J_{[F}{}^A{}_{(F}{}^B{}_{)F}{}^D{}_]}$ is 16 Hz; $J_{[F}{}^A{}_{(F}{}^B{}_{)-H}{}^1{}_]}$ is 7 Hz; $J_{[F}{}^A{}_{(F}{}^B{}_{)-H}{}^2{}_]}$ is 17 Hz; $J_{[F}{}^B{}_{-H}{}^2{}_]}$ is 45 Hz. $^1$H NMR (δ): 1.7 (H$^1$); 5.25 (H$^2$); $J_{[H}{}^1{}_{-H}{}^2{}_]}$ is 7 Hz.

$^{19}$F NMR (δ) of $CH_2{}^1F^CCH_2{}^2CF_2{}^BCF_3{}^A$: 11.5 (3F$^A$); 42.5 (2F$^B$); 147.5 (F$^C$); 55 (F$^B$); J(F$^B$-F$^C$) is 5 Hz; J(F$^B{}_{-H}{}^1$) is 18 Hz; J(F$^C{}_{-H}{}^2$) is 45 Hz; J(F$^C{}_{-H}{}^1$) is 28 Hz.

Example 9

$CH_3CHF_2+CF_2=CF_2 \rightarrow (CF_3CF_2)_2(CH_2)_2+CF_3CF=CHCH_2CF_2CF_3$

Anhydrous HF (80 mL), 1,1-difluoroethane (11 g, 0.2 mol), antimony pentafluoride (45 g, 0.2 mol) and tetrafluoroethylene (40 g, 0.4 mol) were added to a 250 mL steel autoclave. The reaction mixture was agitated at room temperature for 8 hours followed by heating the autoclave in a boiling water bath. The reaction products were collected in a gas-washing bottle containing water. The organic layer was separated, washed with water, dried and distilled to yield a mixture in 50% yield (27 g, b.p. 46 to 58° C.) containing $CF_3CF_2CH_2CH_2CF_2CF_3$ (70%) and $CF_3CF=CHCH_2CF_2CF_3$ (30%). The reaction mixture also contained a small amount of 1-perfuoroethyl-2,2,3,3-tetrafluorocyclobutane.

$^{19}$F NMR (δ) of $CF_3CF_2CH_2CH_2CF_2CF_3$: 11 (CF$_3$); 44.5 (CF$_2$); $J_{H-F}$ was 16 Hz. $^1$H NMR (δ): 2.5 m (2CH$_2$).

Mass spectrum (m/z, assignment, %): 247 (M-F, $C_6H_4F_9{}^+$, 0.1); 227 ($C_6H_3F_8{}^+$, 9.7); 197 ($C_5H_4F_7{}^+$, 18.9); 177 ($C_5H_3F_6{}^+$, 29.6); 157 ($C_5H_2F_5{}^+$, 6.7); 127 ($C_4H_3F_4{}^+$, 24.3); 119 ($C_2F_5{}^+$, 5.6); 113 ($C_3HF_4{}^+$, 31.3); 100 ($C_2F_4{}^+$, 3.9); 77 ($C_3H_3F_2{}^+$, 43.3); 69 (CF$_3{}^+$, 68.4).

$^{19}$F NMR (δ) of $CF_3{}^ACF^B=CH^2CH_2{}^1CF_2{}^CCF_3{}^D$: −1.2 (3F$^a$); 10.5 (3F$^D$); 42.5 (2F$^C$); 55 (F$^B$); J(F$^A$-F$^B$) is 10 Hz. $^1$H NMR (δ): 3.1 (2H$^1$); 5.8 (1H$^2$); J(H$^2$-F$^B$) is 30 Hz; J(H$^1$-H$^2$) is 7.5 Hz; J(H$^1$-F$^C$) is 10 Hz. Raman spectrum (υ, cm$^{-1}$): 1728.

Mass spectrum (m/z, assignment, %): 246 (M$^+$, $C_6H_3F_9{}^+$, 9.6); 227 ($C_6H_3F_8{}^+$, 8.5); 207 ($C_6H_2F_7{}^+$, 2.3); 177 ($C_5H_3F_6{}^+$, 7); 157 ($C_5H_2F_5{}^+$, 0.7); 127 ($C_4H_3F_4{}^+$, 66); 119 ($C_2F_5{}^+$, 2.6); 113 ($C_3HF_4{}^+$, 20.3); 77 ($C_3H_3F_2{}^+$, 100); 69 (CF$_3{}^+$, 68.4).

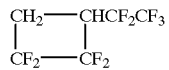

Mass spectrum (m/z, assignment, %): 227 (MF$^+$, $C_6H_3F_8{}^+$, 0.8); 207 ($C_6H_2F_7{}^+$, 1.6); 177 ($C_5H_3F_6{}^+$, 1.8); 157 ($C_5$1.9); 127 ($C_4H_3F_4{}^+$, 4.5); 113 ($C_3HF_4{}^+$, 9.7); 100 ($C_2F_4{}^+$, 13); 77 ($C_3H_3F_2{}^+$, 12); 69 (CF$_3{}^+$, 10.6); 64 ($C_2H_2F_2{}^+$, 100).

Comparative Example C $(CH_3)_2CHF+CF_2=CF_2 \rightarrow$ Tar

Isopropyl fluoride (25 g), antimony pentafluoride (25 g) and tetrafluoroethylene (40 g) were added to a 400 mL Hastelloy™ nickel alloy shaker tube. The reaction mixture was agitated at 25° C. for 12 hours. Only a tarry product was isolated.

Comparative Example D $CF_3CH_2F+CF_2=CF_2 \rightarrow$ PTFE 1,1,1,2-Tetrafluoroethane (50 g), antimony pentafluoride (5 g) and tetrafluoroethylene (40 g) were added to a 400 mL Hastelloy™ nickel alloy shaker tube. The reaction mixture was agitated at 50° C. for 12 hours. The product isolated was polytetrafluoroethylene (PTFE, 10 g) along with recovered $CF_3CH_2F$ (46 g).

Comparative Example E $HCF_2CF_2CH_2F+CF_2=CF \rightarrow$ PTFE 1,1,2,2,3-Pentafluoropropane (55 g), antimony pentafluoride (20 g) and tetrafluoroethylene (30 g) were added to a 400 mL Hastelloy™ nickel alloy shaker tube. The reaction mixture was agitated at 50° C. for 12 hours. The product isolated was polytetrafluoroethylene (PTFE, 20 g) along with recovered $HCF_2CF_2CH_2F$ (32 g).

Comparative Example F $CH_2F_2+CF_2=CF_2 \rightarrow CH_2FCF_2CF_2+CF_2=CF_2 \rightarrow$ PTFE Difluoromethane (55 g), antimony pentafluoride (20 g) and tetrafluoroethylene (TFE, 50 g) were added to a 400 mL Hastelloy™ nickel alloy shaker tube. The reaction mixture was agitated at 50° C. for 12 hours. At this time additional TFE (50 g) was added to the reaction mixture and agitation was continued for 12 hours at 50° C. The product isolated was polytetrafluoroethylene (PTFE, 20 g) along with recovered $CF_3CF_2CH_2F$ (32 g).

What is claimed is:

1. A process for forming an adduct of the formula $RR^1R^2CCR^1R^2F$ or $(FR^1R^2CCRR^2CH_2)_2$ wherein R is selected from the group consisting of $CH_3$, $CH_2F$, $C_2H_4F$ and $F(CF_2)_nCH_2CH_2$ where n is an integer from 1 to 10, each $R^1$ is independently selected from the group consisting of H, Cl, F and $CF_3$ and each $R^2$ is independently selected from the group consisting of H, F and $CF_3$, comprising:

reacting a saturated compound of the formula RF with an olefin of the formula $R^1R^2C=CR^1R^2$ in the liquid phase in the presence of antimony pentafluoride catalyst; provided that when $(FR^1R^2CCR^1R^2CH_2)_2$ is formed, the saturated compound is $CH_3CHF_2$ or $FCH_2CH_2F$ and anhydrous HF is present.

2. The process of claim 1 wherein $CH_2FCF_2CF_3$ is formed.

* * * * *

UNITED STATES PATENT AND TRADEMARK OFFICE
CERTIFICATE OF CORRECTION

PATENT NO. : 6,184,426 B1                                      Page 1 of 1
DATED      : February 6, 2001
INVENTOR(S) : Gennadii G. Belen'kii et al.

It is certified that error appears in the above-identified patent and that said Letters Patent is hereby corrected as shown below:

<u>Title page,</u>
After Inventors, change "Belen'Kill" to -- Belen'kii --.

<u>Column 1,</u>
Line 64, change "$CH_3CHF_2$)" to -- $CH_3CHF_2$ --.

Signed and Sealed this

Fifth Day of February, 2002

Attest:

JAMES E. ROGAN
*Attesting Officer*    *Director of the United States Patent and Trademark Office*